United States Patent [19]

Grindey et al.

[11] Patent Number: 5,565,494

[45] Date of Patent: Oct. 15, 1996

[54] ANTITUMOR COMPOSITIONS AND METHODS OF TREATMENT

[75] Inventors: Gerald B. Grindey; Cora S. Grossman; J. Jeffry Howbert; Karen L. Lobb; James E. Ray; John E. Toth, all of Indianapolis, Ind.

[73] Assignee: Eli Lilly and Company, Indianapolis, Ind.

[21] Appl. No.: 402,407

[22] Filed: Mar. 10, 1995

Related U.S. Application Data

[63] Continuation of Ser. No. 988,618, Dec. 10, 1992, abandoned.

[51] Int. Cl.$^6$ .............. A61K 31/17; A61K 31/18; A61K 31/64; C07C 313/00

[52] U.S. Cl. ................ 514/593; 514/238.2; 514/331; 514/429; 514/592; 514/588; 544/588; 544/163; 546/229; 548/567; 564/39; 564/40

[58] Field of Search ............................ 514/592, 593; 564/40

[56] References Cited

U.S. PATENT DOCUMENTS

| | | | |
|---|---|---|---|
| 3,013,072 | 12/1961 | McLamore et al. | 564/39 |
| 3,083,207 | 3/1963 | Hoehn et al. | 260/319 |
| 3,097,242 | 7/1963 | Hoehn et al. | 564/39 |
| 3,102,115 | 8/1963 | Breuer et al. | 260/239 |
| 3,102,121 | 8/1963 | Breuer et al. | 260/330.5 |
| 3,736,122 | 5/1973 | Tung et al. | 71/103 |
| 3,849,110 | 11/1974 | Soper et al. | 71/103 |
| 4,845,128 | 7/1989 | Harper et al. | 514/592 |
| 5,169,860 | 12/1992 | Mohamadi et al. | 514/415 |

FOREIGN PATENT DOCUMENTS

| | | |
|---|---|---|
| 1208561 | 7/1986 | Canada . |
| 107214 | 9/1983 | European Pat. Off. . |
| 166615 | 1/1986 | European Pat. Off. . |
| 222475 | 5/1987 | European Pat. Off. . |
| 291269 | 11/1988 | European Pat. Off. . |
| 1240866 | 6/1961 | Germany . |
| 1144259 | 2/1963 | Germany . |
| 1159937 | 12/1963 | Germany . |
| 48-26215 | 7/1973 | Japan . |

OTHER PUBLICATIONS

W. J. Ehlhardt, *Drug Metabolism and Disposition,* 19:370 (1991).

J. J. Howbert, et al., *Synthetic Communications,* 20:3193 (1990).

W. J. Ehlhardt, *Drug Metabolism and Disposition,* 19:366 (1991).

J. J. Howbert, et al., *Journal of Medicinal Chemistry,* 33:2393 (1990).

G. B. Grindey, et al., *Proceedings of the American Association of Cancer Research,* 27:277 (Abstract 1099) (1986).

C. W. Taylor, et al., *Journal of Clinical Oncology,* 7:1733 (1989).

J. D. Hainsworth, et al., *Cancer Research,* 49:5217 (1989).

R. Levine, *Diabetes Care,* 7 (Suppl. 1) (1984).

G. F. Holland, et al., *Journal of Medicinal and Pharmaceutical Chemistry,* 3:99 (1961).

P. J. Houghton, et al., *Cancer Chemotherapy and Pharmacology,* 25:84 (1989).

P. J. Houghton, et al., *Cancer Research,* 50:318 (1990).

P. J. Houghton, et al., *Cancer Research,* 50:664 (1990).

P. J. Houghton, et al., *Biochemical Pharmacology,* 39:1187 (1990).

P. H. Dhahir, et al., In *Proceedings of the 36th ASMS Conference on Mass Spectroscopy and Allied Topics,* pp. 972–973 (1988).

G. F. Holland, *Journal of Organic Chemistry,* 26:1662 (1961).

*Chemical Abstracts,* 52:17180; citing Haack, et al., East German Patent 9688, Apr. 21, 1955.

F. Kurzer, *Chemical Reviews,* 50:1 (1952).

G. B. Grindey, et al., In *Proceedings of the American Association for Cancer Research,* 28:309 (Abstract 1224) (1987).

H. Breuer, et al., *Chimie Therapeutique,* Nov./Dec. 1973:659.

L. J. Lerner, et al., *Metabolism,* 14:578 (1965).

*Primary Examiner*—Shailendra Kumar
*Attorney, Agent, or Firm*—Joseph A. Jones; Paul J. Gaylo

[57] ABSTRACT

This invention provides certain benzenesulfonamide derivatives and methods for using them in the treatment of susceptible neoplasms in mammals. Also provided are certain novel pharmaceutical formulations employing these benzenesulfonamide derivatives in combination with a carrier, and processes for preparing the benzenesulfonamide derivatives.

22 Claims, No Drawings

ANTITUMOR COMPOSITIONS AND METHODS OF TREATMENT

This application is a continuation of application Ser. No. 07/988,618, filed on Dec. 10, 1992, now abandoned.

BACKGROUND OF THE INVENTION

In recent years fundamental advances have been made in the development of chemical agents and regimens of therapy to combat neoplastic diseases. Despite these continuing advances, cancers continue to exact intolerable levels of human pain and suffering. The need for new and better methods of treating neoplasms and leukemias continues to fuel efforts to find new classes of antitumor compounds, especially in the area of inoperable or metastatic solid tumors, such as the various forms of lung cancer. Of the one million new cases of cancer diagnosed in the United States each year, more than 90% represent non-hematopoetic tumors, where improvements in five-year survival rates have been modest, at best. B. E. Henderson, et al., *Science*, 254:1131–1137 (1991).

The recent avalanche of information regarding the basic biological processes involved in neoplasms has led to a deeper understanding of the heterogeneity of tumors. Ongoing work has led to the realization that individual tumors may contain many subpopulations of neoplastic cells that differ in crucial characteristics such as karyotype, morphology, immunogenicity, growth rate, capacity to metastasize, and response to antineoplastic agents.

It is because of this extreme heterogeneity among populations of neoplastic cells that new chemotherapeutic agents should have a wide spectrum of activity and a large therapeutic index. In addition, such agents must be chemically stable and compatible with other agents. It is also important that any chemotherapeutic regimen be as convenient and painless as possible to the patient.

This invention reports a series of novel sulfonylureas that are useful in the treatment of solid tumors. These compounds are orally active—which, of course, results in less trauma to the patient—and are relatively non-toxic. These compounds also have an excellent therapeutic index. The compounds and their formulations are novel.

Many sulfonylureas are known in the art. Certain of these compounds are known to have hypoglycemic activities, and have been used medicinally as such agents. In addition, some sulfonylureas have been taught to have herbicidal and antimycotic activities. General reviews of compounds of this structural type are taught by Kurzer, *Chemical Reviews*, 50:1 (1952) and C. R. Kahn and Y. Shechter, *Goodman and Gilman's, The Pharmacological Basis of Therapeutics*, (Gilman, et al., 8th ed. 1990) 1484–1487.

Some diarylsulfonylureas have been reported as being active antitumor agents. e.g., U.S. Pat. No. 5,169,860, of F. Mohamadi and M. Spees, issued Dec. 8, 1992; U.S. Pat. No. 4,845,128 of Harper, et al., issued Jul. 4, 1989; U.S. Pat. No. 5,110,830 of Harper, et al., issued May 5, 1992; U.S. Pat. No. 5,116,874 of G. A. Poore, issued May 26, 1992; European Pat. No. Publication 0467613 (published Jan. 22, 1992); Grindey, et al., *American Association of Cancer Research*, 27:277 (1986); and Houghton, et al., *Cancer Chemotherapy and Pharmacology*, 25:84–88 (1989).

SUMMARY OF THE INVENTION

This invention provides a method of treating a susceptible neoplasm in a mammal which comprises administering to a mammal in need of said treatment an effective amount for treating a susceptible neoplasm of a compound of Formula I:

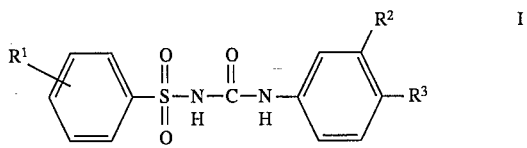

wherein:

$R^1$ is $-NO_2$,

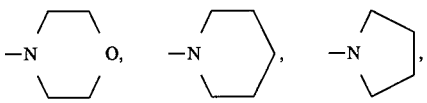

or $-NR^aR^b$, wherein $R^a$ and $R^b$ are independently selected from the group consisting of hydrogen and $C_1$–$C_6$ alkyl; and $R^2$ and $R^3$ are independently selected from the group consisting of hydrogen, halo, $C_1$–$C_6$ alkyl, and trifluoromethyl, provided that no more than one of $R^2$ and $R^3$ can be hydrogen;

with the proviso that, if $R^1$ is $-NO_2$ or $-NH_2$, neither $R^2$ nor $R^3$ can be hydrogen;

or a pharmaceutically acceptable salt or solvate thereof.

This invention also provides novel compounds of Formula II

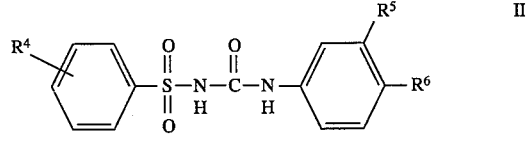

wherein:

$R^4$ is $-NO_2$,

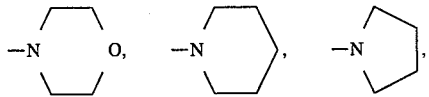

or $-NR^cR^d$, wherein $R^c$ and $R^d$ are independently selected from the group consisting of hydrogen and $C_1$–$C_6$ alkyl; and $R^5$ and $R^6$ are independently selected from the group consisting of hydrogen, halo, $C_1$–$C_6$ alkyl, and trifluoromethyl, provided that no more than one of $R^5$ and $R^6$ can be hydrogen;

with the proviso that if $R^4$ is $-NO_2$ or $-NH_2$, neither $R^5$ nor $R^6$ can be hydrogen;

and the pharmaceutically acceptable salts and solvates thereof. Such compounds are especially useful in the treatment of susceptible neoplasms in mammals.

In addition, this invention provides pharmaceutical formulations comprising an effective amount for treating susceptible neoplasms of a compound of Formula II, in combination with a suitable pharmaceutical carrier, diluent, or excipient. These formulations are useful in the treatment of mammals suffering from susceptible neoplasms.

DETAILED DESCRIPTION AND PREFERRED EMBODIMENTS

As used herein, the term "halo" refers to fluoro, chloro, bromo, and iodo. The term "$C_1$–$C_6$ alkyl" refers to straight and branched chains of 1 to 6 carbon atoms and includes, but is not limited to, methyl, ethyl, propyl, isopropyl, butyl, isobutyl, t-butyl, pentyl, isopentyl, and hexyl.

Preferred methods of treatment employ compounds of Formula I in which $R^1$ is nitro, amino, dimethylamino, methylamino, ethylamino, diethylamino, pyrrolidinyl, piperidinyl, or morpholinyl; and $R^2$ and $R^3$ are independently selected from the group consisting of hydrogen, chloro, fluoro, bromo, iodo, methyl, ethyl, and trifluoromethyl.

Preferred compounds of the instant invention are those of Formula II in which $R^4$ is nitro, amino, dimethylamino, methylamino, ethylamino, diethylamino, pyrrolidinyl, piperidinyl, or morpholinyl; and $R^5$ and $R^6$ are independently selected from the group consisting of hydrogen, chloro, fluoro, bromo, iodo, methyl, ethyl, and trifluoromethyl.

The compounds of Formulas I and II are generally referred to as derivatives of N-[[(substituted phenyl)amino]carbonyl]benzenesulfonamides. Alternatively, the compounds can be referred to as 1-(substituted phenyl)-3-(substituted phenylsulfonyl)ureas or N- and N'-substituted sulfonylureas.

The compounds of formulas I and II can be prepared by methods known in the literature. Generally, these methods involve either the reaction of a sulfonamide with an isocyanate, a reaction of a sulfonylisocyanate with an appropriately substituted aniline, or a reaction of a sulfonylcarbamate with an appropriately-substituted aniline.

A preferred process for preparing a compound of Formula I or Formula II comprises reacting a sulfonylisocyanate of Formula III

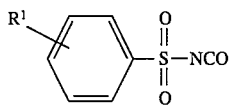

with an aniline derivative of Formula IV

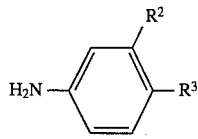

where $R^1$, $R^2$, and $R^3$ are the same as previously defined.

The reaction between compounds III and IV is usually performed using equimolar amounts of the two reactants, although other ratios are operative. The reaction is preferably carried out in a solvent which is nonreactive under the reaction conditions such as benzene, toluene, acetonitrile, diethyl ether, tetrahydrofuran, dioxane, methylene chloride, or acetone.

The reaction can be carried out at temperatures from about 0° C up to about 100° C. At the preferred temperature range of from about 20° C. to about 30° C., the reaction produces a strong exotherm and the reaction is usually complete within one hour. The product thus obtained is recovered by filtration and can be purified, if desired, by any number of methods known to those skilled in the art, such as chromatography or crystallization.

An alternative preferred process for preparing a compound of Formula I comprises reacting an appropriately substituted sulfonamide of Formula V

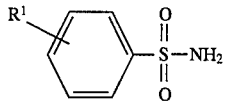

with an isocyanate of Formula VI

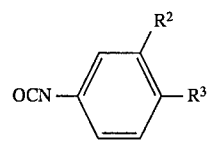

to provide the corresponding compound of Formula I or II.

The reaction is generally performed in a mixture of water and a water-miscible, non-reactive solvent such as tetrahydrofuran or acetone in the presence of a base such as sodium hydroxide, potassium hydroxide, lithium hydroxide, sodium methoxide, sodium hydride and the like. Generally, an equimolar or slight molar excess of VI is employed, although other ratios are operative. Usually, the amount of base used is approximately equimolar to the amount of V. The reaction is generally carried out from about 0° C. up to about 100° C. At the preferred temperature of about 20° C. to about 30° C., the reaction is usually complete within about three hours.

A preferred process for preparing a compound of Formula I or II involves reacting a sulfonamide of Formula V with an alkyl haloformate of the formula $XCOOR^7$, where X is bromo or chloro and $R^7$ is $C_1-C_3$ alkyl, to provide the carbamate of Formula VII and then reacting it with an aniline derivative of Formula IV to provide the corresponding product of Formula I or II

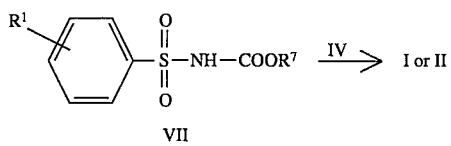

The transformation of V into VII is usually accomplished in a non-reactive solvent, such as acetone or methyl ethyl ketone, in the presence of an acid scavenger, such as an alkali metal carbonate, for example potassium carbonate. A molar excess of the haloformate is usually added, although other ratios are operative. The reaction mixture is heated to a temperature from about 30° C. up to the reflux temperature of the mixture for a period of about 1–6 hours to provide the desired intermediate VII. Intermediate carbamate VII and the substituted aniline IV are then heated together in an inert high-boiling solvent, such as dioxane, toluene, or diglyme, at temperatures from about 50° C. up to the reflux temperature of the mixture to provide the desired product of Formula I or II.

The carbamate of Formula VII can also be synthesized by the procedure described by Arkins and Burgess. G. Arkins and E. Burgess, *Journal of the American Chemical Society*, 94:6135 (1972). In this process triethylamine and a substituted aniline are mixed in the presence of a solvent such as benzene. To this mixture a sulfamoyl chloride is added to produce the carbamate of Formula VII.

Intermediates III, IV, V, and VI and any other reagents required for these methods of preparation are commercially available, are known in the literature, or can be prepared by methods known in the art.

This invention includes methods employing the pharmaceutically acceptable salts of the Formula I compounds, and includes the pharmaceutically acceptable salts of the Formula II compounds. The Formula I and II compounds can react with basic materials such as alkali-metal or alkaline-earth-metal hydroxides, carbonates, and bicarbonates including, without limitation, sodium hydroxide, sodium carbonate, potassium hydroxide, calcium hydroxide, lithium hydroxide, etc. to form pharmaceutically acceptable salts such as the corresponding sodium, potassium, lithium, or calcium salt. Organic bases can also be used, including primary, secondary, and tertiary alkyl amines such as methylamine, triethylamine, and the like.

This invention further relates to the pharmaceutically acceptable solvates of the compounds of Formulas I and II. The Formula I and II compounds can combine with solvents such as water, methanol, ethanol and acetonitrile to form pharmaceutically acceptable solvates such as the corresponding hydrate, methanolate, ethanolate and acetonitrilate.

The terms and abbreviations used in the instant examples have their normal meanings unless otherwise designated. For example "° C." refers to degrees Celsius; "N" refers to normal or normality; "mmole" refers to millimole; "g" refers to gram; "ml" means milliliter; "M" refers to molar or molarity; "FDMS" refers to field desorption mass spectrometry; and "NMR" refers to nuclear magnetic resonance.

The following examples further illustrate the preparation of the compounds of Formula I and Formula II. These examples are illustrative only and are not intended to limit the scope of the invention in any way.

EXAMPLE 1

Preparation of N-[[(4-chlorophenyl)amino]carbonyl]-4-(dimethylamino)benzenesulfonamide A 1 liter 3-neck round bottom flask, fitted with a mechanical stirrer, Dean-Stark trap and condenser was charged with N,N-dimethyl-N'-carbethoxysulfanilamide (32.7 g, 120 mmoles), 4-chloroaniline (17.2 g, 132 mmoles) and 600 ml of toluene. The N,N-dimethyl-N'-carbethoxysulfanilamide was prepared in substantial accordance with procedures known in the art. See, e.g., G. Arkins and E. Burgess, *Journal of the American Chemical Society*, 94:6135 (1972). The mixture was stirred and heated under reflux for 2 hours, removing 50 ml of toluene/ethanol azeotrope via the Dean-Stark trap. After cooling in an ice-bath, the resulting solid was filtered off and rinsed with 100 ml toluene. The crude product was slurried in 350 ml of ethanol for 2 hours, filtered (100 ml ethanol and 500 ml diethyl ether rinse) and vacuum-dried to give 23.3 g of the title product, a 55% yield.

Analysis of the product gave the following results: mp=189°–190° C.; $R_f$(1/9 MeOH/CHCl$_3$)=0.54; $^1$H NMR (300 MHz, d$_6$-DMSO) δ 2.98 (s, 6H, 2NCH$_3$), 6.75 (d, 2H, J=9.1 Hz, Ar-H), 7.27 (d, 2H, J=8.9 Hz, Ar-H), 7.33 (d, 2H, J=9.1 Hz, Ar-H), 7.67 (d, 2H, J=8.9 Hz, Ar-H), 8.78 (s, 1H, exchanges with D$_2$O, NH) and 10.42 (bs, 1H, exchanges with D$_2$O, SO$_2$NH); IR (KBr) 3293, 2896, 1700, 1601, 1519, 1445, 1155, 1090 and 916 cm$^{-1}$; FDMS(MeOH) m/e 353,355 (M$^+$).

Analysis for $C_{15}H_{16}ClN_3O_3S$:

Theory: C, 50.92; H, 4.56; N, 11.88

Found: C, 51.07; H, 4.66; N, 11.98.

EXAMPLE 2

Preparation of N-[[(3,4-dichlorophenyl)amino]carbonyl]-4-(dimethylamino)benzenesulfonamide The procedure of Example 1 was followed, using N,N-dimethyl-N'-carbethoxysulfanilamide (32.7 g, 120 mmoles), 3,4-dichloroaniline (21.8 g, 132 mmoles) and 600 ml of toluene. The crude product precipitated from solution after 2 hours, and was purified as in Example 1 to give 24.9 g (53%) pure title product.

Analysis of the product gave the following results: mp=194°–195° C.; $R_f$(1/9 MeOH/CHCl$_3$)=0.36; $^1$H NMR (300 MHz, d$_6$-DMSO) δ 62.98 (s, 6H, 2NCH$_3$), 6.75 (d, 2H, J=9.1 Hz, Ar-H), 7.24(m, 1H, Ar-H), 7.47 (d, 1H, J=8.8 Hz, Ar-H), 7.67–7.70 (m, 3H, Ar-H), 8.98 (s, 1H, exchanges with D$_2$O, NH) and 10.61 (bs, 1H, exchanges with D$_2$O, SO$_2$NH); IR (KBr) 3319, 3242, 1707, 1602, 1511, 1450, 1376, 1154, 1091, 1039, 813 and 669 cm$^{-1}$; FDMS(MeOH) m/e 387, 389,391 (M$^+$).

Analysis for $C_{15}H_{15}Cl_2N_3O_3S$:

Theory: C, 46.40; H, 3.89; N, 10.82

Found: C, 46.21; H, 3.90; N, 10.60.

EXAMPLE 3

Preparation of N-[[(4-chlorophenyl)amino]carbonyl]-4-(diethylamino)benzenesulfonamide 4-Fluorobenzenesulfonamide (3.0 g, 17.1 mmoles) and diethylamine (26.6 ml) were mixed together in 20 ml of dimethyl sulfoxide. The reaction mixture was heated to 135° C. in a sealed pressure tube and maintained at this temperature for about 14 hours.

The mixture was then allowed to cool to room temperature. Water (400 ml) was then added to the reaction. This mixture was extracted twice with ethyl acetate (1×400 ml, 1×100 ml). The combined organic layers were extracted with 1N hydrochloric acid (300 ml), and the organic layers discarded.

The acid layer was neutralized with 300 ml of 1N sodium hydroxide and extracted with ethyl acetate. After passage through sodium sulfate, the organic solvents were removed by evaporation, to provide 1.13 g of light brownish solid. The solid was then re-dissolved in 50 ml of ethyl acetate and extracted with 1N hydrochloric acid (50 ml). To the aqueous layer was added 50 ml of 1N sodium hydroxide, causing a precipitate. This mixture was extracted with ethyl acetate (3×50 ml). The combined organic layers were evaporated to give 0.99 g (25%) of 4-(diethylamino)-benzenesulfonamide as a light brown solid.

This benzenesulfonamide (0.99 g, 4.3 mmoles) was dissolved in acetone (4.3 ml) to which was then added 1.0N sodium hydroxide (4.4 ml). To this mixture was added 4-chlorophenylisocyanate (0.68 g, 4.4 mmoles), dissolved in 4.3 ml of acetone. This mixture was allowed to stir at room temperature for about 15 minutes. A solid was then removed from the reaction mixture by filtration. To the filtrate was added 1.0N hydrochloric acid (4.4 ml), causing separation of a brown oil. Water (5 ml) was then added and the mixture stirred until the oil had converted to a solid. The solid was collected and washed three times with water.

The solid was recrystallized using toluene (20 ml), followed by three washes with toluene, resulting in 1.18 g (71%) of the desired title product.

Analysis of the product gave the following results: $^1$H NMR (300 MHz, d$_6$-DMSO) δ 1.10 (t, 6H, J=7 Hz, 2CH$_3$), 3.39 (q, 4H, J=7 Hz, 2 CH$_2$), 6.74 (d, 2H, J=9 Hz, Ar-H), 7.29 (d, 2H, J=9 Hz, Ar-H), 7.36 (d, 2H, J=9 Hz, Ar-H), 7.67 (d, 2H, J=9 Hz, Ar-H), 8.80 (s, 1H, NH) and 10.40 (brs, 1H, SO$_2$NH).

FDMS m/e 381, 383,384 (M$^+$).

Analysis for $C_{17}H_{20}ClN_3O_3S$:

Theory: C, 53.47; H, 5.28;N, 11.00

Found: C, 53.73; H, 5.43;N, 10.86.

EXAMPLE 4

Preparation of N-[[(4-chlorophenyl)amino]carbonyl]-3-(dimethylamino)benzenesulfonamide To a solution of 3-fluorobenzenesulfonamide (3.0 g, 17.1 mmoles) in 15 ml of dimethyl sulfoxide was added 29 ml of dimethylamine (40% w/w in water). This mixture was sealed in a pressure tube and heated to 138° C. for 16 hours. The reaction mixture was allowed to cool to room temperature, and then added to 500 ml of water. The mixture was extracted with ethyl acetate (1×400 ml, 1×100 ml).

The combined organic layers were washed with 300 ml of 1N hydrochloric acid. The acid wash was neutralized with 300 ml of 1N sodium hydroxide and extracted with ethyl acetate (300 ml). The organic layer was dried over anhydrous sodium sulfate, filtered, and concentrated under vacuum to yield 1.83 g (9.1 mmoles, 53%) of 3-(dimethylamino)benzenesulfonamide as a white solid.

The 3-(dimethylamino)benzenesulfonamide was dissolved in acetone (9.1 ml) to which was added 9.3 ml of 1N sodium hydroxide. To this mixture was added 4-chlorophenylisocyanate (1.43 g, 9.3 mmoles) dissolved in 9.1 ml of acetone. This mixture was stirred for 45 minutes at room temperature and then filtered. The filtrate was acidified using 1N hydrochloric acid (9.3 ml) and stirred for 2 hours, resulting in a precipitate. The solid was collected, washed thrice with water, and recrystallized using heated toluene (150 ml) and ethyl acetate (25 ml), followed by filtration and cooling.

The collected crystals were washed with cool toluene (three times) and dried in a vacuum oven, yielding 2.09 g (65%) of the desired title compound.

Analysis of the product gave the following results: $^1$H NMR (300 MHz, $d_6$-DMSO) δ 62.96 (s, 6H, 2CH$_3$), 6.98 (m, 1H, Ar-H), 7.20 (m, 2H, Ar-H), 7.28–7.42 (m, 5H, Ar-H), 8.98 (s, 1H, NH), and 10.68 (brs, 1H, SO$_2$NH)

Analysis for $C_{15}H_{16}ClN_3O_3S$:

Theory: C, 50.92; H, 4.56;N, 11.88

Found: C, 50.70; H, 4.51;N, 11.65.

EXAMPLE 5

Preparation of N-[[(4-chlorophenyl)amino]carbonyl]-4-(ethylamino)benzenesulfonamide To a solution of 4-fluorobenzenesulfonamide (3.0 g, 17.1 mmoles) in dimethyl sulfoxide (20 ml) was added ethylamine (20.8 ml of a 70% (w/w) solution in water). The reaction mixture was heated at 105° C. for 15 hours in a pressure tube and then cooled to room temperature. The mixture was added to 500 ml of water and extracted with ethyl acetate, first using 400 ml, then with 100 ml. The combined organic layers were washed with 500 ml of water, dried over anhydrous sodium sulfate, filtered and concentrated under vacuum.

The 4-(ethylamino)benzenesulfonamide was recrystallized using 200 ml of toluene. The collected crystals were washed with cool toluene (three times) to yield 1.56 g (7.8 mmoles, 46%).

The 4-(ethylamino)benzene-sulfonamide was dissolved in 7.8 ml of acetone with 7.9 ml of 1N sodium hydroxide added. To this mixture was added 4-chlorophenylisocyanate (1.22 g, 7.9 mmoles), dissolved in 7.8 ml of acetone. This reaction mixture was allowed to stir for 25 minutes at room temperature, then filtered, with a small amount of an acetone:water (1:1) mixture being used to rinse out the flask and wash the filtered solid. The filtrate was acidified with 1N hydrochloric acid (7.9 ml) and stirred for about an hour until the initially separated oil had changed to a solid.

The solid was collected and rinsed three times with water. The solid was recrystallized using hot toluene (250 ml) and ethyl acetate (10 ml), filtered while still hot, then allowed to cool. The collected crystals were washed three times with cool toluene and dried in a vacuum oven, resulting in 1.77 g (64%) of the desired title compound.

Analysis of the product gave the following results: $^1$H NMR (300 MHz, $d_6$-DMSO) δ 1.16 (t, 3H, J=7 Hz, CH$_3$), 3.10 (pentet, 2H, J=7 Hz, CH$_2$), 6.62 (d, 2H, J=9 Hz, Ar-H), 6.63 (brs, 1H, EtNH), 7.29 (d, 2H, J=10 Hz, Ar-H), 7.36 (d, 2H, J=10 Hz, Ar-H), 7.62 (d, 2H, J=9 Hz, Ar-H), 8.78 (s, 1H, ArNHCO) and 10.37 (brs, 1H, SO$_2$NH)

Analysis for $C_{15}H_{16}ClN_3O_3S$:

Theory: C, 50.92; H, 4.56;N, 11.88

Found: C, 51.17; H, 4.63;N, 11.87.

EXAMPLE 6

Preparation of N-[[(4-chlorophenyl) amino]-carbonyl]-4-(4-morpholinyl) benzenesulfonamide 4-Fluorobenzenesulfonamide (5.50 g, 31.4 mmoles) was dissolved in 100 ml of morpholine (99.6 g, 1.14 moles) and was refluxed for 3 days. The solvent was removed by evaporation, yielding an orange oil. Methylene chloride (100 ml) was added, causing the oil to solidify. The solid was collected by filtration, then heated in 100 ml of ethanol. After cooling, the solid was collected by filtration, yielding 5.59 g (73%) of 4-(4-morpholinyl)benzenesulfonamide as a white solid.

In 16 ml of acetone, 3.36 g of 4-(4morpholinyl)benzenesulfonamide (15 moles) was suspended. To this suspension, 16 ml of 1N sodium hydroxide was added, followed by 32 ml of water, resulting in a cloudy solution. This solution was rendered clear by addition of another 32 ml of acetone and 24 ml of water.

4-Chlorophenylisocyanate (2.61 g, 17 moles) was dissolved in 16 ml of acetone and was then added dropwise to the sulfonamide solution. The mixture was then stirred overnight at room temperature, resulting in the formation of a white solid.

The solid was removed by filtration. The filtrate was neutralized with 1N hydrochloric acid (16 ml), resulting in the formation of another white solid. The mixture was diluted with 125 ml of water and stirred for 30 minutes. The solid was collected by filtration, washed with water (3×15 ml) and dried in vacuum, yielding 3.92 g (66%) of the title compound.

Analysis of the product gave the following results: $^1$H NMR (270 MHz, $d_6$-DMSO) δ 53.28 (m, 4H, 2NCH$_2$), 3.73 (m, 4H, 2 OCH$_2$), 7.06 (d, 2H, J=9 Hz, Ar-H), 7.31 (d, 2H, J=8 Hz, Ar-H), 7.38 (d, 2H, J=8 Hz, Ar-H), 7.76 (d, 2H, J=9 Hz, Ar-H), 8.89 (s, 1H, NH) and 10.54 (brs, 1H, SO$_2$NH)

Analysis for $C_{17}H_{18}ClN_3O_4S$:

Theory: C, 51.58; H 4.58;N, 10.61; S, 8.10

Found: C, 51.44; H, 4.58;N, 10.44; S, 7.87.

EXAMPLE 7

Preparation of N-[[(4-chlorophenyl) amino]-carbonyl]-4-(1-pyrrolidinyl) benzenesulfonamide In a mixture of 33 ml of acetone, 22 ml of acetonitrile, and 30 ml of water was dissolved 2.68 g (11.8 mmoles) of 4-(1-pyrrolidinyl)benzenesulfonamide. To this mixture, 1.0N sodium hydroxide (11.8 ml) was added and the solution was briefly stirred.

4-Chlorophenylisocyanate (1.99 g, 13 mmoles) was dissolved in 10 ml of acetone and then added to the sulfonamide solution over the course of one minute. This reaction mixture was allowed to stir overnight.

The mixture was filtered to remove a small amount of solid and the filtrate was acidified to pH=5.5 with 1.0N hydrochloric acid (11.8 ml added), producing a fine white precipitate. The solid was recovered by filtration, yielding 3.31 g (74%) of the title compound. Nuclear magnetic resonance assays confirmed the identity of the isolated material as being the title compound.

Analysis for $C_{17}H_{18}ClN_3O_3S$:

Theory: C, 53.75; H 4.78;N, 11.06; Cl, 9.33

Found: C, 53.13; H, 4.70;N, 10.02; Cl, 11.43.

EXAMPLE 8

Preparation of N-[[(3,4-dichlorophenyl) amino]-carbonyl]-4-(amino) benzenesulfonamide To a solution of p-aminobenzenesulfonamide (8.6 g, 50 mmoles) in 50 ml of 1N aqueous sodium hydroxide and 50 ml of acetone was added a solution of 3,4-dichlorophenyl-isocyanate (9.4 g, 50 mmoles) in 50 ml of acetone, dropwise over 30 minutes. Three hours later the reaction mixture was treated with 50 ml of 1N aqueous hydrochloric acid, dropwise over 30 minutes. The reaction mixture was diluted with 100 ml of water and cooled in an ice bath while being subjected to vigorous magnetic stirring. The resulting solid was collected by filtration, rinsed with 100 ml of water and dried. Purification of a portion of this crude solid by silica gel flash chromatography (5% methanol/$CH_2Cl_2$) provided purified product (2.8 g), which was suspended in water, collected by filtration and air dried.

Analysis of the product gave the following results: mp=194°–196° C.; $R_f$(⅓ MeOH/$CHCl_3$)=0.21; $^1$H NMR (300 MHz, $d_6$-DMSO) δ 6.11(s, 2H, exchanges with $D_2O$, Ar-$NH_2$), 6.58 (d, 2H, J=8.7 Hz, Ar-H), 7.24 (dd, 1H, J=8.8, 2.7 Hz, Ar-H), 7.47 (d, 1H, J=8.8 Hz, Ar-H), 7.54 (d, 2H, J=8.7 Hz, Ar-H) , 7.68 (d, 1H, J=2.4 Hz, Ar-H) , 8.93 (s, 1H, exchanges with $D_2O$, NH), and 10.52 (bs, 1H, exchanges with $D_2O$, $SO_2NH$), IR (KBr) 3366, 3302, 1703, 1642, 1594, 1522, 1455, 1316, 1156, 1087 and 1042 cm$^{-1}$; FDMS (MeOH) m/e 359, 361, 363 (M$^+$).

Analysis for $C_{13}H_{11}Cl_2N_3O_3S$:

Theory: C, 43.35; H 3.08;N, 11.67

Found: C, 43.15; H, 3.21;N, 11.48.

EXAMPLE 9

Preparation of N-[[(4-chlorophenyl)amino]carbonyl -(methylamino)benzenesulfonamide Preparation of 4-(N-methyl-N-ethoxycarbonyl)aminobenzenesulfonamide hemihydrate Ethyl N-methyl-N-phenylcarbamate (15.5 g, 86.5 mmoles), prepared as described in N. Leister, et al., *Journal of Organic Chemistry*, 1958, 1152, was added in portions under nitrogen purge to a flask containing chlorosulfonic acid (30 ml, 450 mmoles). After stirring vigorously for 90 minutes the reaction mixture was quenched by the addition of crushed ice and extracted with methylene chloride (3×100 ml). The combined organic extract was dried over calcium sulfate, filtered and evaporated to an oil. The crude sulfonyl chloride was stirred with 250 ml of ammonium hydroxide for 3 hours and the product sulfonamide was collected on a filter, rinsed with water (250 ml) and vacuum dried (5.5 g, 25% ).

Analysis of this intermediate product gave the following results: mp=138°–139° C.; $R_f$(1/1 EtOAc/hexane) =0.28; $^1$H NMR (300 MHz, $d_6$-DMSO) δ 1.17 (t, 3H, J=7.0 Hz, $CH_2CH_3$), 3.24 (s, 3H, $NCH_3$), 4.08 (q, 2H, J=7.0 Hz, $CH_2CH_3$), 7.33 (s, 2H, exchanges with D2O, $SO_2NH_2$), 7.49 (d, 2H, J=8.6 Hz, Ar-H) and 7.76 (d, 2H, J=8.6 Hz, Ar-H); UV(EtOH) $\lambda_{max}$ (ε) 251.8 (12941) and 202.8 (14996) nm; IR (KBr) 3335, 1685, 1377, 1333, 1157 and 833 cm$^{-1}$; FDMS (MeOH) m/e 258 (M$^+$).

Analysis for $C_{10}H_{14}N_2O_4S$:

Theory: C, 46.50; H 5.46;N, 10.84

Found: C, 46.73; H, 5.45;N, 10.66.

The procedure of Example 8 was then followed, using the 4-(N-methyl-N-ethoxycarbonyl)-aminobenzenesulfonamide hemihydrate prepared supra (7.4 g, 28.6 mmoles), 28.6 ml of 1N NaOH solution and 4-chlorophenylisocyanate (4.5 g, 28.7 mmoles) to yield 5.9 g (50%) of the corresponding sulfonylurea.

Analysis of the product gave the following results: mp=131°–133° C.; $R_f$(THF)=0.56; $^1$H NMR (300 MHz, $d_6$-DMSO) δ 1.18 (t, 3H, J=7.0 Hz, $CH_2CH_3$), 3.26 (s, 3H, $NCH_3$), 4.09 (q, 2H, J=7.0 Hz, $CH_2CH_3$), 7.31 (m, 4H, Ar-H), 7.55 (d, 2H, J=8.7 Hz, Ar-H), 7.89 (d, 2H, J=8.7 Hz, Ar-H), 9.04 (s, 1H, exchanges with $D_2O$, NH) and 10.7 (bs, 1H, exchanges with $D_2O$, $SO_2NH$); UV(EtOH) $\lambda_{max}$(ε) 249.0 (35538) and 204.8 (38013) nm; IR (KBr) 3329, 1727, 1675, 1605, 1545, 1175, 1094 and 830 cm$^{-1}$; FDMS (MeOH) m/e 411, 413 (M$^+$).

Analysis for $C_{17}H_{18}ClN_3O_5S \cdot 0.25 C_4H_{10}O$:

Theory: C, 50.23; H, 4.80;N, 9.76

Found: C, 50.07; H, 4.77;N, 9.71.

The sulfonylurea formed supra (5.4 g, 13.1 mmoles) was heated at reflux in 2N aqueous potassium hydroxide solution (60 ml, 120 mmoles) for 2 hours. After cooling in an ice bath, the reaction mixture was quenched by the addition of 5N aqueous hydrochloric acid solution (24 ml). Filtration and drying gave the crude product, which was purified by treatment with 25 ml of 1N sodium hydroxide solution and 100 ml of water followed by filtration to remove the insoluble material. Treatment of this filtrate with 25 ml 1N hydrochloric acid solution followed by filtration and drying gave 2.1 g of the title product (47%).

Analysis of the title product gave the following results: mp=173°–174° C.; $R_f$(EtOAc)=0.45; $^1$H NMR (300 MHz, $d_6$-DMSO) δ 2.70 (d, 3H, J=4.0 Hz, $NHCl_3$), 6.57 (d, 2H, J=8.8 Hz, Ar-H), 6.67 (m, 1H, $NHCH_3$), 7.27 (d, 2H, J=8.7 Hz, Ar-H), 7.35 (d, 2H, J=8.7 Hz, Ar-H), 7.63 (d, 2H, J=8.8 Hz, Ar-H), 8.78(s, 1H, exchanges with $D_2O$, NH) and 10.4 (bs, 1H, exchanges with $D_2O$, $SO_2NH$); UV(EtOH) $\lambda_{max}$(ε) 278.8 (26112), 249.4 (24189) and 203.2 (37423) nm; IR (KBr) 3431, 3279, 1690, 1605, 1523, 1164, 1092, 822 and 688 cm$^{-1}$; FDMS (MeOH) m/e 339, 341 (M$^+$).

Analysis for $C_{14}H_{14}ClN_3O_3S \cdot 0.5\ H_2O$:

Theory: C, 48.21; H 4.33;N, 12.05

Found: C, 48.18; H, 4.13;N, 12.01.

EXAMPLE 10

Preparation of N-[[(3,4-dichlorophenyl) amino]-carbonyl-4-(methylamino) benzenesulfonamide The procedure of Example 8 was followed using 4-(N-methyl-N-ethoxycarbonyl) aminobenzenesulfonamide hemihydrate (5.3 g, 20.5 mmoles), 20.5 ml of 1N sodium hydroxide and 3,4-dichlorophenylisocyanate (4.0 g, 20.6 mmoles) to yield 8.5 grams (92%) of the intermediate sulfonylurea.

Analysis of the product gave the following results: mp=164°–165° C.; $R_f$(THF)=0.87; $^1$H NMR (300 MHz, $d_6$-DMSO) δ 1.18 (t, 3H, J=7.0 Hz, $CH_2CH_3$), 3.27 (s, 3H, $NCH_3$), 4.09 (q, 2H, J=7.0 Hz, $CH_2CH_3$), 7.26 (m, 1H, Ar-H), 7.52 (d , 1H, J=8.8 Hz, Ar-H), 7.59 (d, 2H, J=8.8 Hz, Ar-H), 7.70 (s, 1H, Ar-H), 7.91 (d, 2H, J=8.8 Hz, Ar-H), 9.20 (s, 1H, exchanges with $D_2O$, NH) and 11.0 (bs, 1H, exchanges with $D_2O$, $SO_2NH$); UV(EtOH) $\lambda_{max}$(ε) 251.4 (30129) and 209.4 (41332) nm; IR (KBr) 1723, 1660, 1594, 1528, 1347, 1041, 872 and 709 cm$^{-1}$; FDMS (MeOH) m/e 445, 447, 449 (M$^+$).

Analysis for $C_{17}H_{17}ClN_3O_3S \cdot 0.33\ H_2O$:

Theory: C, 45.75; H 3.84;N, 9.41

Found: C, 45.63; H, 3.87;N, 9.25.

The procedure of Example 9 was then followed, using the carbamate synthesized supra (7.5 g, 16.8 mmoles) and 80 ml of 2N potassium hydroxide solution (160 mmoles) to yield 1.93 g (31%) of product.

Analysis of the product gave the, following results: mp=155°–156° C.; $R_f$(THF)=0.56; $^1$H NMR (300 MHz, $d_6$-DMSO) δ 2.67 (d, 3H, J=4.0 Hz, NHCH$_3$), 6.53 (d obscuring bs, 2H+1H, J=8.8 Hz, 2Ar-H, NHCH$_3$), 7.21 (d, 1H, J=8.9 Hz, Ar-H), 7.41 (d, 1H, J=8.9 Hz, Ar-H), 7.58 (d, 2H, J=8.8 Hz, Ar-H), 7.69 (s, 1H, Ar-H), 8.90 (s, 1H, exchanges with D$_2$O, SO$_2$NH) and 10.5 (bs, 1H, exchanges with D$_2$O, NH); UV(MeOH/pH=7 buffer, 1:1) $\lambda_{max}$(ε) 265.8 (32610), 257.2 (33806) and 209.0 (39683) nm; IR (KBr) 3450, 3250, 1740, 1510, 1175 and 1060 cm$^{-1}$; FDMS (MeOH)m/e 373, 375, 377 (M$^+$).

Analysis for C$_{14}$H$_{13}$Cl$_2$N$_3$O$_3$S.0.33 H$_2$O:

Theory: C, 44.23; H 3.62;N, 11.05

Found: C, 44.04; H, 3.37;N, 11.00.

EXAMPLE 11

Preparation of N-[[(3,4-dichlorophenyl)amino]-carbonyl-4-(methylethylamino)benzenesulfonamide Preparation of N-ethyl-N-methyl-N'-carbethoxysulfanilamide This intermediate was synthesized essentially as described in Burgess et.al., supra, using N-ethyl-N-methylaniline (10.5 ml, 69.8 mmoles), carbethoxysulfamoyl chloride (12.8 g, 68.2 mmoles) and triethylamine (9.5 ml, 68.2 mmoles) in 200 ml of benzene to yield 11.9 g (61%) of the subtitle product.

Analysis of this product gave the following results: mp=147°–150° C.; $R_f$(1/1 EtOAc/hexane)=0.38; $^1$H NMR (300 MHz, $d_6$-DMSO) δ 1.02–1.11 (t overlapping t, 6H, OCH$_2$CH$_3$ and NCH$_2$CH3), 2.93 (s, 3H, NCH$_3$), 3.44 (q, 2H, J=7.0 Hz, NCH$_2$CH$_3$), 3.96 (q, 2H, J=7.0 Hz, OCH$_2$CH$_3$), 6.73 (d, 2H, J=9 Hz,Ar-H), 7.60 (d, 2H, J=9 Hz, Ar-H), and 11.5 (bs, 1H, exchanges with D$_2$O, NH); UV(EtOH) $\lambda_{max}$(ε) 286.5 (23988) and 219.0 (8704) nm; IR (KBr) 3240, 1750, 1595, 1231, 1141, 1090 and 821 cm$^{-1}$; FDMS (MeOH) m/e 286 (M$^+$).

Analysis for C$_{12}$H$_{18}$N$_2$O$_4$S:

Theory: C, 50.33; H 6.34;N, 9.78

Found: C, 50.28; H, 6.52;N, 9.85.

Next, the method of Example 1 was followed, using N-ethyl-N-methyl-N'-carbethoxysulfanilamide (9.4 g, 32.8 mmoles) and 3,4-dichloroaniline (6.0 g, 36.3 mmoles) in 150 ml of toluene to yield 10.0 g (76%) of the title product.

Analysis of the product gave the following results: mp=147°–150° C.; $R_f$(1/1 EtOAc/hexane)=0.38; $^1$H NMR (300 MHz, $d_6$-DMSO) δ 1.04 (t, 3H, J=7.0 Hz, NCH$_2$CH$_3$), 2.93 (s, 3H, NCH$_3$), 3.44 (q, 2H, J=7.0 Hz, NCH$_2$CH$_3$), 6.74 (d, 2H, Ar-H), 7.24 (m, 1H, Ar-H), 7.47 (d, 1H, J=8.7 Hz, Ar-H), 7.66 (d overlapping s, 3H, Ar-H), 8.97 (s, 1H, exchanges with D$_2$O, NH) and 10.6 (bs, 1H, exchanges with D$_2$O, SO$_2$NH); UV(MeOH/pH=7 buffer, 1:1) $\lambda_{max}$(ε) 280.0 (27280), 58.0 (28746) and 210.0 (37068) nm; IR (KBr) 3356, 3261, 1709, 1588, 1515, 1453, 1152 and 811 cm$^{-1}$; FDMS (MeOH) m/e 401, 403,405 (M$^+$).

Analysis for C$_{16}$H$_{17}$Cl$_2$N$_3$O$_3$S:

Theory: C, 47.77; H 4.26;N, 10.45

Found: C, 47.98; H, 4.23;N, 10.28.

EXAMPLE 12

Preparation of N-[[(3,4-dichlorophenyl)amino]-carbonyl-4-(diethylamino)benzenesulfonamide Preparation of N, N-diethyl-N'-carbethoxysulfanilamide The method of Example 11 was followed, using N,N-diethylaniline (10.7 ml, 67 mmoles), carbethoxysulfamoyl chloride (12 g, 64 mmoles) and triethylamine (8.9 ml, 63.8 mmoles) in 150 ml of benzene to yield 13.6 g (71%) of the intermediate product.

Analysis of the product gave the following results: mp=120°–121° C.; $R_f$(1/1 EtOAc/hexane)=0.49; $^1$H NMR (300 MHz, $d_6$-DMSO) δ 1.06–1.11 (t overlapping t, 9H, OCH$_2$CH$_3$, 2NCH$_2$CH$_3$), 3.35 (q, 4H, J=7.0 Hz, 2NCH$_2$CH$_3$), 3.96 (q, 2H, J=7.0 Hz, OCH$_2$CH$_3$), 6.71 (d, 2H, J=9.0 Hz, Ar-H), 7.58 (d, 2H, J=9.0 Hz, Ar-H) and 11.5 (bs, 1H, exchanges with D$_2$O, NH); UV(EtOH) $\lambda_{max}$(ε) 284.5 (23324) and 202.5 (16968) nm; IR (KBr) 3261, 1751, 1593, 1139 and 824 cm$^{-1}$; FDMS (MeOH) m/e 300 (M$^+$).

Analysis for C$_{13}$H$_{20}$N$_2$O$_4$S:

Theory: C, 51.98; H 6.71;N, 9.33

Found: C, 51.75; H, 6.59;N, 9.54.

Next, the method of Example 1 was followed, using N,N-diethyl-N'-carbethoxysulfanilamide (9.0 g, 30 mmoles) and 3,4-dichloroaniline (6.0 g, 36.3 mmoles) in 150 ml of toluene. After 2 hours, the solvent was removed in vacuo and the solid triturated with diethyl ether (200 ml), collected by filtration, and vacuum dried to yield 10 g of crude product. The solid was stirred with ethanol (40 ml) for one hour, filtered, and vacuum dried to yield 6.7 g (54%) of product.

Analysis of the product gave the following results: mp=164°–165° C.; $R_f$(9/1 CHCl$_3$/MeOH)=0.41; $^1$H NMR (300 MHz, $d_6$-DMSO) δ 1.08 (t, 6H, J=7.0 Hz, 2NCH$_2$CH$_3$), 3.37(q, 4H, J=7.0 Hz, 2NCH$_2$CH$_3$), 6.71 (d, 2H, J=8.7 Hz, Ar-H), 7.24 (m, 1H, Ar-H), 7.47 (d, 1H, J=8.7 Hz, Ar-H), 7.66 (d overlapping s, 3H, Ar-H), 8.95 (s, 1H, exchanges with D$_2$O, NH) and 10.6 (bs, 1H, exchanges with D$_2$O, SO$_2$NH); UV(MeOH/pH=7 buffer, 1:1) $\lambda_{max}$(ε) 283.6 (27991), 258.4 (26478) and 209.4 (35937) nm; IR (KBr) 33521, 1704, 1594, 1518, 1450, 1196, 1165, 1095 and 814 cm$^{-1}$; FDMS (MeOH) m/e 415, 417, 419 (M$^+$).

Analysis for C$_{17}$H$_{19}$ClN$_3$O$_3$S:

Theory: C, 49.05; H 4.60;N, 10.09

Found: C, 48.77; H, 4.60;N, 9.91.

The compounds of Formula I and Formula II have been shown to be active against transplanted human tumors in vivo. To demonstrate the anti-tumor activity of the compounds of Formula I, these compounds were tested in mice bearing different allograft and xenograft tumors.

Two of the tumor models used for showing the antineoplastic activity of the sulfonylureas of this invention were the human colon xenografts, HXGC3 and VRC5. J. A. Houghton and D. M. Taylor, *British Journal of Cancer*, 37:213–223 (1978). These tumors were obtained from St. Jude's Children's Research Hospital and have been widely used as human tumor models.

A third tumor model employed C3H mice bearing the widely used allograft 6C3HED lymphosarcoma, also known as the Gardner lymphosarcoma (GLS). The 6C3HED lymphosarcoma was obtained from the Division of Cancer Treatment, National Cancer Institute, Tumor Bank, maintained at E.G. and G. Mason Research (Worcester, Mass.).

First passage tumors were stored in liquid nitrogen, using standard techniques. The transplanted tumor was reestablished from the Tumor Bank every six months or as needed. The tumor was maintained by serial passage twice weekly in the host mice.

In the procedures utilized here, the tumor was removed from passage animals and minced into 1- to 3-mm cubic fragments using sterile techniques. Tumor pieces were checked for sterility using both Antibiotic Medium 1 and Brain Heart Infusion (Difco, Detroit, Mich.). The xenograft tumor pieces were implanted into the recipient CD1 Nu/Nu mice subcutaneously in an axillary site by trochar. The allograft 6C3HED tumor pieces were implanted into the recipient C3H mice in an analogous fashion.

Drug therapy on the appropriate schedule was initiated seven days after tumor implantation. The compound being tested was mixed with 2.5% Emulphor EL620 from GAF Corporation (1:40 dilution in 0.9% saline). The total dosage volume for each administration was 0.5 ml. All animals were weighed at the beginning and end of administration of the subject compounds. Food and water were provided ad libitum.

Each control group and each dosage level of the treated groups consisted of 9 or 10 mice selected at random from the pool of implanted animals. The formulations were administered orally by gavage with the use of an 18-gauge needle. Compounds were dosed daily for 10 days for the studies using the human tumor xenografts and 8 days for the studies using the allograft.

The tumor was measured five days after treatment ended with two dimensional measurements (width and length) of the tumor taken using digital electronic calipers interfaced to a microcomputer. J. F. Worzalla, et Investigational New Drugs, 8:241–251 (1990). Tumor weights were calculated from these measurements using the following formula:

$$\text{Tumor weight (mg)} = \frac{\text{tumor lingth (mm)} \times [\text{tumor width (mm)}]^2}{2}$$

At least one control group of an equal number of mice was treated with the same volume of 2.5% Emulphor only. The percent inhibition is determined by subtracting the ratio of the mean tumor size of the test group relative to the control group from one and multiplying the result by 100.

The results of several experiments in mice bearing the HXGC3 and VRC5 human colon adenocarcinomas and the 6C3HED lymphosarcoma when the Formula I compounds were administered orally are provided in Table I. In the table, Column 1 refers to the example number of the compound tested; Column 2 describes the particular human tumor xenograft or mouse allograft being studied; Column 3 gives the dosage level of the compound of Formula I in milligrams per kilogram of body weight; Column 4 describes the percent inhibition of tumor growth; and Column 5 tallies the number of mice which died during the course of the experiment relative to the total number of animals in the group.

TABLE I

Activity of the Compounds of Formula I Against Allograft and Xenograft Tumors In Vivo

| Example No. | Tumor | Dosage (mg/kg) | Percent Inhibition | Toxic/Total |
|---|---|---|---|---|
| 1 | 6C3HED | 600 | Toxic | 10/10 |
|  |  | 300 | 100 | 0/10 |
|  |  | 150 | 100 | 0/10 |
|  |  | 75 | 99 | 0/10 |
|  |  | 37.5 | 80 | 0/10 |
| 2 | 6C3HED | 160 | 97 | 0/10 |
|  |  | 80 | 89 | 0/10 |
|  |  | 40 | 51 | 0/10 |
|  |  | 20 | 35 | 0/10 |
|  | HXGC3 | 1200 | 100 | 1/10 |
|  |  | 600 | 100 | 1/10 |

TABLE I-continued

Activity of the Compounds of Formula I Against Allograft and Xenograft Tumors In Vivo

| Example No. | Tumor | Dosage (mg/kg) | Percent Inhibition | Toxic/Total |
|---|---|---|---|---|
|  |  | 300 | 100 | 0/10 |
|  |  | 150 | 100 | 0/10 |
|  | VRC5 | 1200 | 100 | 0/10 |
|  |  | 600 | 100 | 1/10 |
|  |  | 300 | 100 | 0/10 |
|  |  | 150 | 100 | 0/10 |
| 4 | 6C3HED | 300 | 95 | 0/10 |
|  |  | 150 | 73 | 0/10 |
| 5 | 6C3HED | 300 | 74 | 0/10 |
| 6 | 6C3HED | 300 | 38 | 0/10 |
|  |  | 150 | 17 | 0/10 |
| 7 | 6C3HED | 300 | 48 | 0/10 |
|  |  | 150 | 44 | 0/10 |
| 8 | 6C3HED | 775 | 100 | 1/10 |
|  |  | 388 | 29 | 0/10 |
|  |  | 194 | 34 | 0/10 |
| 9 | 6C3HED | 600 | 100 | 0/10 |
|  |  | 300 | 100 | 0/10 |
| 10 | 6C3HED | 600 | 100 | 2/10 |
|  |  | 300 | 100 | 0/10 |
| 11 | 6C3HED | 300 | 96 | 1/10 |
|  |  | 150 | 71 | 0/10 |
| 12 | 6C3HED | 300 | 70 | 0/10 |
|  |  | 150 | 54 | 0/10 |

The compounds of Formula I are usually administered in the form of pharmaceutical compositions. These compositions can be administered by a variety of routes including oral, rectal, transdermal, subcutaneous, intravenous, intramuscular, and intranasal. Such compositions are useful in treating solid tumors including carcinomas such as ovarian, non-small cell lung, gastric, pancreatic, prostate, renal cell, breast, colorectal, small cell lung, melanoma, and head and neck; and sarcomas such as Kaposi's sarcoma and rhabdomyosarcoma.

The Formula I compounds are preferably administered in the form of oral pharmaceutical compositions. Such compositions are prepared in a manner well known in the pharmaceutical art and comprise at least one active compound.

In another aspect, the present invention also includes novel pharmaceutical compositions which contain, as the active ingredient, the compounds of Formula II associated with pharmaceutically acceptable carriers. In making the compositions of the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are effective over a wide dosage range. For examples, dosages per day normally fall within the range of about 0.5 to about 600 mg/kg of body weight. In the treatment of adult humans, the range of about 1 to about 50 mg/kg, in single or divided dose, is preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way.

Typical compositions of this invention are described in the following examples:

Formulation Example 1

Hard gelatin capsules containing the following ingredients are prepared:

| Ingredient | Quantity (mg/capsule) |
| --- | --- |
| N-[[(3,4-dichlorophenyl)amino]carbonyl]-4-(ethylmethylamino)benzenesulfonamide | 250.0 |
| Starch | 305.0 |
| Magnesium stearate | 5.0 |

The above ingredients are mixed and filled into hard gelatin capsules in 560 mg quantities.

Formulation Example 2

A tablet formula is prepared using the ingredients below:

| Ingredient | Quantity (mg/tablet) |
| --- | --- |
| N-[[(4-chlorophenyl)amino]carbonyl]-3-(diethylamino)benzenesulfonamide | 250.0 |
| Cellulose, microcrystalline | 400.0 |
| Colloidal silicon dioxide | 10.0 |
| Stearic acid | 5.0 |

The components are blended and compressed to form tablets, each weighing 665 mg.

Formulation Example 3

A dry powder inhaler formulation is prepared containing the following components:

| Ingredient | Weight % |
| --- | --- |
| N-[[(3,4-difluorophenyl)amino]carbonyl]-4-(1-piperidinyl)benzenesulfonamide | 5 |
| Lactose | 95 |

The active mixture is mixed with the lactose and the mixture is added to a dry powder inhaling appliance.

Formulation Example 4

Tablets, each containing 60 mg of active ingredient, are prepared as follows:

| Ingredient | Quantity (mg/tablet) |
| --- | --- |
| N-[[(3,4-dichlorophenyl)amino]carbonyl]-4-(dimethyiamino)benzenesuifonamide | 60.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 150 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50°–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

Formulation Example 5

Capsules, each containing 80 mg of medicament are made as follows:

| Ingredient | Quantity (mg/capsule) |
| --- | --- |
| N-[[(3,4-difluorophenyl)amino]carbonyl]-3-nitrobenzenesulfonamide | 80.0 mg |
| Starch | 109.0 mg |
| Magnesium stearate | 1.0 mg |
| Total | 190.0 mg |

The active ingredient, cellulose, starch, and magnesium stearate are blended, passed through a No. 20 mesh U.S. sieve, and filled into hard gelatin capsules in 190 mg quantities.

Formulation Example 6

Suppositories, each containing 225 mg of active ingredient are made as follows:

| Ingredient | Amount |
| --- | --- |
| N-[[(3,4-dichlorophenyl)amino]carbonyl]-4-(1-pyrrolidinyl)benzenesulfonamide | 225 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
| --- | --- |
| N-[[4-methylphenyl)amino]carbonyl]-4-(4-morpholinyl)benzenesulfonamide | 50.0 mg |
| Xanthan gum | 4.0 mg |
| Sodium carboxymethyl cellulose (11%) microcrystalline cellulose (89%) | 50.0 mg |
| Sucrose | 1.75 g |
| Sodium benzoate | 10.0 mg |
| Flavor | q.v. |
| Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

Capsules, each containing 150 mg of medicament, are made as follows:

| Ingredient | Quantity (mg/capsule) |
| --- | --- |
| N-[[(4-trifluoromethylphenyl)amino]carbonyl]-3-(propylamino)benzenesulfonamide | 150.0 mg |
| Starch | 407.0 mg |
| Magnesium stearate | 3.0 mg |
| Total | 560.0 mg |

The active ingredient, cellulose, starch, and magnesium stearate are blended, passed through a No. 20 mesh U.S. sieve, and filled into hard gelatin capsules in 560 mg quantities.

We claim:

1. A compound of the formula

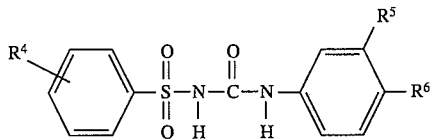

wherein:
$R^4$ is

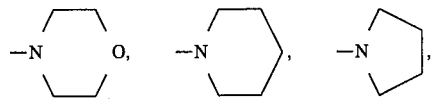

—$NR^cR^d$, where $R^c$ and $R^d$ are independently selected from the group consisting of hydrogen and $C_1$–$C_6$ alkyl, provided that no more than one of $R^c$ and $R^d$ can be hydrogen; and $R^5$ and $R^6$ are independently selected from the group consisting of hydrogen, halo, methyl, and trifluoromethyl, provided that no more than one of $R^5$ and $R^6$ can be hydrogen;

or a pharmaceutically acceptable salt or solvate thereof.

2. A compound as claimed in claim 1 wherein $R^6$ is halo.

3. A compound as claimed in claim 1 wherein $R^6$ is chloro.

4. A compound as claimed in claim 3 that is N-[[(4-chlorophenyl)amino]carbonyl]-4-(dimethylamino)-benzenesulfonamide.

5. The compound as claimed in claim 3 that is N-[[(3,4-dichlorophenyl)amino]carbonyl]-4-(dimethylamino)-benzenesulfonamide.

6. The compound as claimed in claim 3 that is N-[[(4-chlorophenyl)amino]carbonyl]-4-(methylamino)-benzenesulfonamide.

7. The compound as claimed in claim 3 that is N-[[(4-chlorophenyl)amino]carbonyl]-3-(dimethylamino)benzenesulfonamide.

8. A method of treating a susceptible neoplasm in a mammal which comprises administering to a mammal in need of said treatment an effective amount for treating the susceptible neoplasm of a compound of the formula

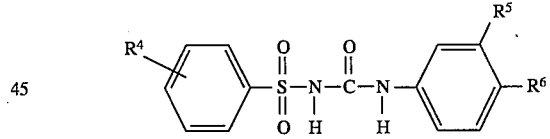

wherein:
$R^4$ is

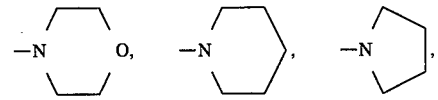

—$NR^cR^d$, where $R^c$ and $R^d$ are independently selected from the group consisting of hydrogen and $C_1$–$C_6$ alkyl, provided that no more than one of $R^c$ and $R^d$ can be hydrogen; and $R^5$ and $R^6$ are independently selected from the group consisting of hydrogen, halo, methyl, and trifluoromethyl, provided that no more than one of $R^5$ and $R^6$ can be hydrogen;

or a pharmaceutically acceptable salt or solvate thereof.

9. A method as claimed in claim 8 employing a compound wherein $R^3$ is halo.

10. A method as claimed in claim 9 employing a compound wherein $R^3$ is chloro.

11. The method as claimed in claim 10 employing N-[[(4-chlorophenyl)amino]carbonyl]-4-(dimethylamino)-benzenesulfonamide.

12. The method as claimed in claim 10 employing N-[[(3,4-dichlorophenyl)amino]carbonyl]-4-(dimethylamino)-benzenesulfonamide.

13. The method as claimed in claim 10 employing N-[[(4-chlorophenyl)amino]-carbonyl]-4-(methylamino)-benzenesulfonamide.

14. The method as claimed in claim 10 employing N-[[(4-chlorophenyl)amino]carbonyl]-3-(dimethylamino)-benzenesulfonamide.

15. A pharmaceutical formulation comprising an effective amount of a compound of the formula

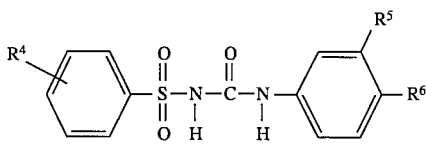

wherein:
R$^4$ is

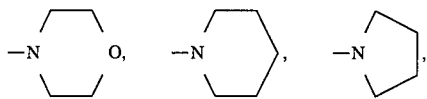

—NR$^c$R$^d$, where R$^c$ and R$^d$ are independently selected from the group consisting of hydrogen and C$_1$–C$_6$ alkyl, provided that no more than one of R$^c$ and R$^d$ can be hydrogen; and R$^5$ and R$^6$ are independently selected from the group consisting of hydrogen, halo, methyl, and trifluoromethyl, provided that no more than one of R$^5$ and R$^6$ can be hydrogen;

or a pharmaceutically acceptable salt or solvate thereof.

16. A formulation as claimed in claim 15 employing a compound wherein R$^6$ is halo.

17. A formulation as claimed in claim 16 employing a compound wherein R$^6$ is chloro.

18. The formulation as claimed in claim 17 employing the compound N-[[(4-chlorophenyl)amino]carbonyl]4-(dimethylamino)benzenesulfonamide.

19. The formulation as claimed in claim 17 employing the compound N-[[(3,4-dichlorophenyl)amino]carbonyl]-4-(dimethylamino)benzenesulfonamide.

20. The formulation as claimed in claim 17 employing the compound N-[[(4-chlorophenyl)amino]carbonyl]-4-(methylamino)benzenesulfonamide.

21. The formulation as claimed in claim 17 employing N-[[(4-chlorophenyl)amino]carbonyl]-3 -(dimethylamino)benzenesulfonamide.

22. A method as claimed in claim 8 wherein said susceptible neoplasm is a colorectal or lymphatic neoplasm.

* * * * *

UNITED STATES PATENT AND TRADEMARK OFFICE
CERTIFICATE OF CORRECTION

PATENT NO. : 5,565,494

DATED : October 15, 1996

INVENTOR(S) : Gerald B. Grindey, et al.

It is certified that error appears in the above-identified patent and that said Letters Patent is hereby corrected as shown below:

In Claim 1, Column 18, lines 10-14, please delete the phrase

In Claim 8, Column 18, lines 50-54, please delete the phrase

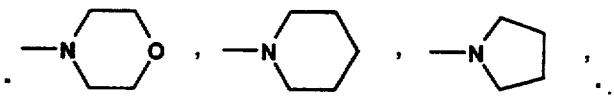

In Claim 15, Column 19, lines 17-24, please delete the phrase

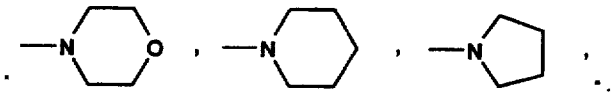

In Claim 21, Column 20, lines 26-27, please delete the space (gap) between the phrase N-[[(4-chlorophenyl)amino]carbonyl]-3 and -(dimethylamino)benzenesulfonamide.

Signed and Sealed this

Twenty-fifth Day of March, 1997

*Attest:*

BRUCE LEHMAN

*Attesting Officer*  Commissioner of Patents and Trademarks